(12) United States Patent
Harsy

(10) Patent No.: US 7,959,657 B1
(45) Date of Patent: Jun. 14, 2011

(54) PORTABLE THERMAL THERAPEUTIC APPARATUS AND METHOD

(76) Inventor: Douglas R. Harsy, Southlake, TX (US)

( * ) Notice: Subject to any disclaimer, the term of this patent is extended or adjusted under 35 U.S.C. 154(b) by 505 days.

(21) Appl. No.: 10/886,413

(22) Filed: Jul. 7, 2004

(51) Int. Cl.
*A61F 7/00* (2006.01)
(52) U.S. Cl. ........................ 607/104; 607/105; 607/112
(58) Field of Classification Search .................. 607/104, 607/108–112, 114
See application file for complete search history.

(56) References Cited

U.S. PATENT DOCUMENTS

| | | | |
|---|---|---|---|
| 5,097,829 A | 3/1992 | Quisenberry | |
| 5,174,285 A | 12/1992 | Fontenot | |
| 5,865,841 A | 2/1999 | Kolen et al. | |
| 5,895,418 A * | 4/1999 | Saringer | 607/104 |
| 5,948,012 A * | 9/1999 | Mahaffey et al. | 607/104 |
| 5,964,092 A | 10/1999 | Tozuka et al. | |
| 5,967,225 A | 10/1999 | Jenkins | |
| 5,980,561 A * | 11/1999 | Kolen et al. | 607/104 |
| 5,989,285 A | 11/1999 | DeVilbiss et al. | |
| 6,295,819 B1 * | 10/2001 | Mathiprakasam et al. | 62/3.3 |
| 6,569,572 B1 * | 5/2003 | Ochiai et al. | 429/303 |
| 6,572,638 B1 * | 6/2003 | Dae et al. | 607/96 |
| 6,685,731 B2 * | 2/2004 | Kushnir et al. | 607/104 |
| 6,840,955 B2 * | 1/2005 | Ein | 607/108 |
| 6,878,156 B1 * | 4/2005 | Noda | 607/106 |
| 6,942,015 B1 * | 9/2005 | Jenkins | 165/46 |
| 2005/0066401 A1 | 3/2005 | Feher | |
| 2005/0143797 A1 | 6/2005 | Parish et al. | |
| 2008/0058911 A1 | 3/2008 | Parish et al. | |
| 2009/0069731 A1 | 3/2009 | Parish et al. | |

OTHER PUBLICATIONS

Alsius® Intravascular Temperature Management, "*EMS Coolers/Warmers*", [online], http://www.alsius.com/products/ems.html, Retrieved Jan. 22, 2008, 2 pages.
Alsius®, "*Cool or Warm IV Fluid. Anytime. Anywhere.*", [online], http://www.alsius.com/PDF/104144%20B%20-%20IV%20Fluid%20Cooler-Warmer%20Unit%20Sales%20Sheet.pdf, Retrieved Jan. 22, 2008, 2 pages.

* cited by examiner

*Primary Examiner* — Henry M Johnson, III
*Assistant Examiner* — Aaron Roane
(74) *Attorney, Agent, or Firm* — Dan Brown Law Office; Daniel R. Brown

(57) ABSTRACT

A portable thermal therapeutic apparatus, adapted to transfer heat between a creature and the atmosphere by circulating heat transfer fluid within a conduit held in contact with the creature. The apparatus includes a housing with a support structure that is particularly adapted for portable use. A heat pump is disposed within the housing, and operates to transfer heat between a first portion and a manifold. A heat sink is thermally coupled to the first portion, and transfers heat between the first portion and the atmosphere. A pump is disposed within the housing and circulates the fluid through the manifold and the conduit. A power supply is disposed within the housing and drives the pump, thereby causing the fluid to circulate within the manifold and the conduit. The power supply is also provides direct current to the heat pump, thereby causing heat to flow from the manifold to the first portion.

8 Claims, 6 Drawing Sheets

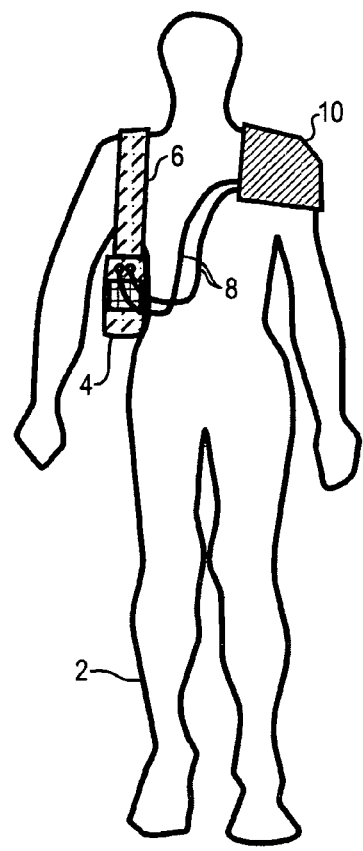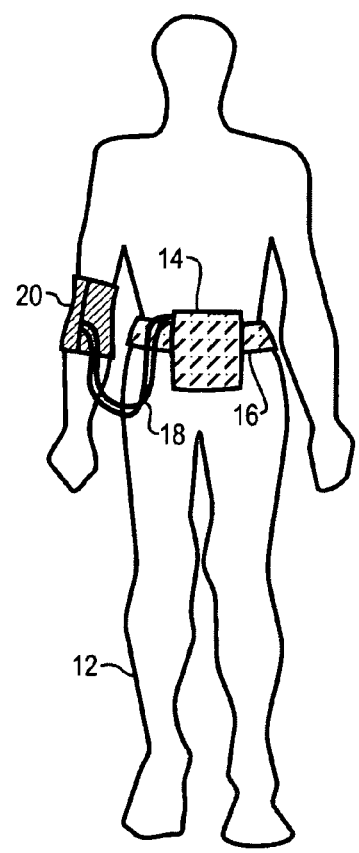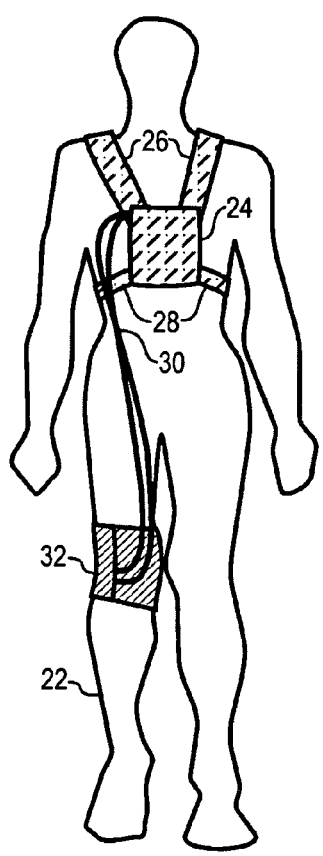
Fig. 1                Fig. 2                Fig. 3
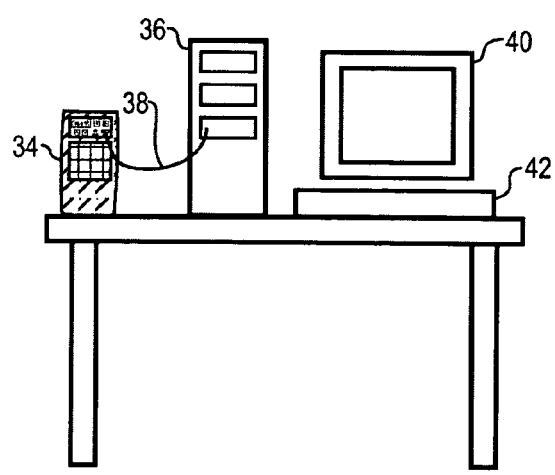
Fig. 4

PORTABLE THERMAL THERAPEUTIC APPARATUS AND METHOD

BACKGROUND OF THE INVENTION

1. Field of the Invention

The present invention relates to hot and cold therapy apparatus and methods. More specifically, the present invention relates to portable solid-state thermal therapeutic apparatus and methods employing heat pump heat transfer devices and a circulating working fluid to cool and warm body parts.

2. Description of the Related Art

The benefits of hot and cold therapy in treatment of various human and animal conditions are well documented. Various apparatus have been devised to achieve the desired transfer of heat between a creature, human or animal, and such an apparatus. Classic examples are the hot water bottle and the ice pack. Modern medicine now recommends specific amounts of heat transfer for specific durations of time as are indicated for various physical ailments and conditions. For example, soft tissue injuries often indicate cold therapy immediately after injury for several hours. Lower back pain can be treated with heat therapy to alleviate pain.

Traditionally, hot and cold therapy has been accomplished with the affected individual in a fixed position. Such thinking corresponded to the concept of limited physical movement of the patient during therapy or recovery from injury. However, patients often desire some degree of mobility during therapy. Movement and mobility during hot and cold therapy, generally thermal therapy, is acceptable in the case where there is no undue strain to the affected portion of the patient's body. In fact, some movement of the affected area is tolerable, and sometimes desirable. Given the need and desire for mobility during thermal therapy, some devices and apparatus have been brought to market. One example is the ice chest and bladder cold therapy system. In the ice chest system, the user carries and insulated chest that contains a mixture of ice and water, along with a pump and battery. A pair of hoses is coupled the chest and pump and to a body-worn bladder, which is held against the affected portion of the patient's body. The patient is able to carry the chest as they move about. Some significant limitations of this approach are the size and bulk of the systems vis-à-vis carrying it, and the lack of control over temperature.

Efforts to reduce the size and weight, and enhance the controllability of portable thermal therapy systems have not kept pace with the needs and desires of patients, therapists and doctors. The use of Peltier effect solid thermoelectric modules (hereinafter "TEM" or "TEM's") has been considered, as is evident in the prior art. For example, U.S. Pat. No. 5,097,829 to Quisenberry for "Temperature Controlled Cooling System" teaches a TEM heat pump cold therapy device with a temperature control system. A circulating fluid is used with a thermal blanket. A pump circulates the fluid, and a fin type heat exchanger removes the waste heat. A pulse width modulated electrical signal powers the TEM pump to control temperature. However, the Quisenberry device is only for fixed operation, receiving substantial power input from the utility power grid.

Another reference is U.S. Pat. No. 5,174,285 to Fontenot for "Localized Heat Transfer Device." Fontenot teaches a TEM pump cooler that employs a hermetically sealed fluid circuit and a peristaltic pump. The closed loop system prevents the working fluid from being contaminated. A reversible cassette can be changed to make it a heat therapy unit. However, the Fontenot device is also only powered from the utility grid, and is of substantial size and power consumption.

Another reference is U.S. Pat. No. 5,895,418 to Saringer for "Device for Producing Cold Therapy." Saringer teaches a TEM cooling device similar to Quisenberry, but adds a thermal reserve in the form of a tank of liquid. The physical structure of the heat exchanger is such that the device can be made somewhat smaller than the prior designs. However, Saringer is still a fixed position device, not contemplating the aforementioned desired mobility aspects. Thus it can be understood, there is a need in the art for a compact and portable thermal therapy device capable of both hot and cold therapy in such a configuration as to enable comfortable portable operation.

SUMMARY OF THE INVENTION

A portable thermal therapeutic apparatus, adapted to transfer heat between a creature and the atmosphere by circulating heat transfer fluid within a conduit held in contact with the creature is taught. The apparatus includes a housing with a support structure that is particularly adapted for portable use. A heat pump is disposed within the housing, and operates to transfer heat between a first portion and a manifold. A heat sink is thermally coupled to the first portion, and transfers heat between the first portion and the atmosphere. A pump is disposed within the housing and circulates the fluid through the manifold and the conduit. A power supply is disposed within the housing and drives the pump, thereby causing the fluid to circulate within the manifold and the conduit. The power supply is also provides direct current to the heat pump, thereby causing heat to flow from the manifold to the first portion.

In a specific embodiment of the foregoing invention, a fan is included, which receives power from the power supply. The fan circulates the atmosphere about the heat sinking, thereby be enabling heat transfer by forced convection. In another embodiment, the power supply includes a rechargeable battery. An external power source input connector may be added to the power supply. The external input is used to couple external power from the utility power grid or from a power outlet of a vehicular power supply.

In another specific embodiment, the apparatus includes a fluid reservoir disposed within the housing that is coupled along the conduit to hold a reserve of fluid therein. The housing may be insulated against the flow of heat. The housing may be padded on its exterior surfaces. In a refinement to the invention, the apparatus further includes a display and an actuator. A controller in the housing operates to interpret actuation of the actuator as input of a temperature set point. The controller then displays the temperature set point on the display. In other specific embodiments, the support structure is a shoulder strap or a belt. In a particular embodiment, the housing and the support structure are configured as a backpack.

In order to minimize the size and weight of the apparatus, a piezoelectric pump is employed in one embodiment. In another embodiment, the apparatus further includes a temperature sensor positioned to sense the temperature of the fluid as it exits the manifold. The temperature sensor has a temperature signal output, and the power supply operates to adjust the direct current flow to the heat pump in response to the temperature signal. In another embodiment, the power supply operates to reverse the polarity of the direct current, thereby reversing the heat flow through the heat pump, causing heat to flow from the first portion to the manifold.

In a particular embodiment, the housing is divided into a first housing portion attached to a first location along the support structure and a second housing portion attached to a second location along the support structure. The pump, the heat pump, and the heat sink are located within the first housing portion, and the power supply is located in the second housing portion. This embodiment allows the weight and bulk of the apparatus to be distributed about a user's body.

In another specific embodiment, the apparatus further includes a temperature sensor positioned to sense the temperature of the fluid as it exits the manifold. The temperature sensor outputs a temperature signal. A controller receives the temperature signal. The controller causes the power supply to adjust the direct current flow to cause the temperature signal to reach a predetermined set-point temperature. In another refinement of the invention, the controller adjusts the direct current flow to cause the temperature signal to reach a plurality of predetermined set-point temperatures over a plurality of time intervals. A communications port is coupled to the controller in another embodiment. The controller is remotely programmable through the communications port.

In an illustrative embodiment of the present invention, a portable thermal therapeutic apparatus, adapted to transfer heat between a creature and the atmosphere by circulating heat transfer fluid within a conduit held in contact with the creature is taught. The apparatus includes a housing with a padded exterior covering that is insulated against the flow of heat, and has a support structure adapted for portable use. Plural Peltier effect heat pumps, having a combined cooling capacity of approximately twenty watts at a differential temperature of approximately thirty-five degrees Celsius, are disposed within the housing. They operate to transfer heat between a first portion and a manifold. A heat sink is thermally coupled to the first portion, and transfers heat between the first portion and the atmosphere. A fan is positioned to circulate the atmosphere about the heat sink, thereby enabling heat transfer by forced convection. A piezoelectric pump that has a flow capacity greater than one-half liter-per-minute at five pounds per square inch pressure is disposed within the housing. The pump circulates the fluid through the manifold and the conduit. A fluid reservoir is also disposed within the housing, and is coupled between the piezoelectric pump and the conduit. A power supply, with a lithium-ion rechargeable battery of approximately one-hundred eighty watt-hour capacity and an external power source input connector for coupling external power from the utility power grid or from a power outlet of a vehicular power supply is disposed within the housing. The power supply drives the pump, thereby causing the fluid to circulate within the manifold and the conduit. The power supply also drives the fan and further provides the direct current to the heat pump, thereby causing heat to flow from the manifold to the first portion. A temperature sensor is positioned to sense the temperature of the fluid as it exits the manifold. A temperature signal is output from the sensor. A display and an actuator are disposed on an exterior surface of the housing. A controller is coupled to the temperature sensor, the display, the actuator, and the power supply. In operation, the controller interprets actuations of the actuator as a plural temperature set points and plural time interval inputs. The controller displays the temperature set points and time intervals on the display. The controller receives the temperature signal and adjusts the direct current flow to cause the temperature signal to reach the plurality of predetermined set point temperatures over the plurality of time intervals. The controller also causes the power supply to reverse the polarity of the direct current, thereby reversing the heat flow through the heat pump, causing heat to flow from the first portion to the manifold. A communications port is coupled to the controller so that the controller is remotely programmable to receive the plurality of predetermined set-point temperatures and the plurality of time intervals.

The present invention also teaches a method of applying thermal therapy using a portable apparatus enclosed in a housing with a support structure. The method includes the steps of supporting the housing from the user's body by engaging the support structure to the user's body, and placing a conduit having heat transfer fluid therein into contact with the body of a user, thereby transferring heat between the user and the heat transfer fluid. Also, the steps of coupling the conduit to a pump and a manifold of a heat pump disposed within the housing, and applying power to the pump, by a power supply disposed within the housing, thereby circulating the heat transfer fluid through the conduit and the manifold. Finally, delivering direct current to the heat pump, by the power supply, thereby transferring heat between the heat transfer fluid in the manifold and the heat sink.

In a refinement to the foregoing method, and additional step of blowing the atmosphere against the heat sink using a fan disposed within the housing, thereby transferring heat by forced convection is added. In another refinement, the method includes the additional step of delivering electric current to the power supply from a rechargeable battery. A further refinement of the method includes the additional step of recharging the battery from the utility power grid or operating the apparatus from a power outlet of a vehicular power supply. Another embodiment adds the step of circulating the heat transfer fluid through a fluid reservoir disposed within the housing. To improve thermal efficiency, the step of insulating the housing against the flow of heat is added.

In a specific embodiment of the foregoing method, the method includes the additional steps of entering a set-point operating temperature using an actuator disposed on the housing, and displaying the set-point temperature on a display disposed on the housing. In another embodiment, the steps of sensing the temperature of the heat transfer fluid as it exits the manifold, and adjusting the direct current flow to the heat pump in response to the sensed temperature are added. In another refinement, the step of reversing the polarity of the direct current, by the power supply, thereby reversing the heat flow through the heat pump is added.

In another specific embodiment of the method, the method includes the further steps of sensing the temperature of the heat transfer fluid as it exits the manifold, and adjusting the flow of direct current to the heat pump, thereby causing the temperature to reach a predetermined set-point. In another improvement, the further step of adjusting the flow of direct current, thereby causing the temperature to reach a plurality of predetermined set-point temperatures over a plurality of time intervals is added. In another specific embodiment of the method, the method includes the further steps of sensing the temperature of the heat transfer fluid as it exits the manifold, and adjusting the flow rate of the pump, thereby causing the temperature to reach a predetermined set-point.

BRIEF DESCRIPTION OF THE DRAWINGS

FIG. 1 is a drawing of a shoulder-worn thermal therapeutic apparatus according to an illustrative embodiment of the present invention.

FIG. 2 is a drawing of a belt-worn thermal therapeutic apparatus according to an illustrative embodiment of the present invention.

FIG. 3 is a drawing of a backpack-worn thermal therapeutic apparatus according to an illustrative embodiment of the present invention.

FIG. 4 is a drawing of a computer programming station for a thermal therapeutic apparatus according to an illustrative embodiment of the present invention.

DESCRIPTION OF THE INVENTION

Figure 5:
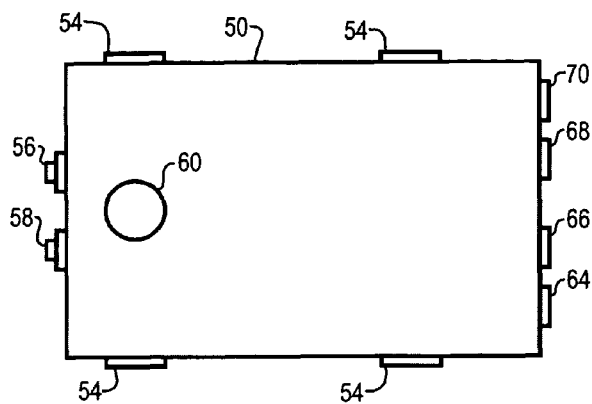
FIG. 5 is a top view drawing of a thermal therapeutic apparatus according to an illustrative embodiment of the present invention.
Figure 6:
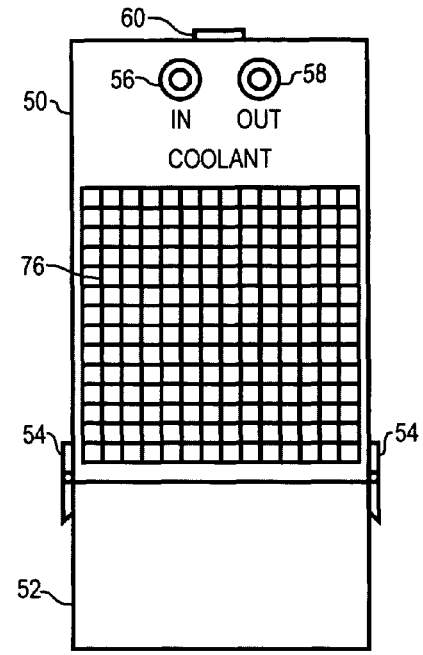
FIG. 6 is an end view drawing of a thermal therapeutic apparatus according to an illustrative embodiment of the present invention.
Figure 7:
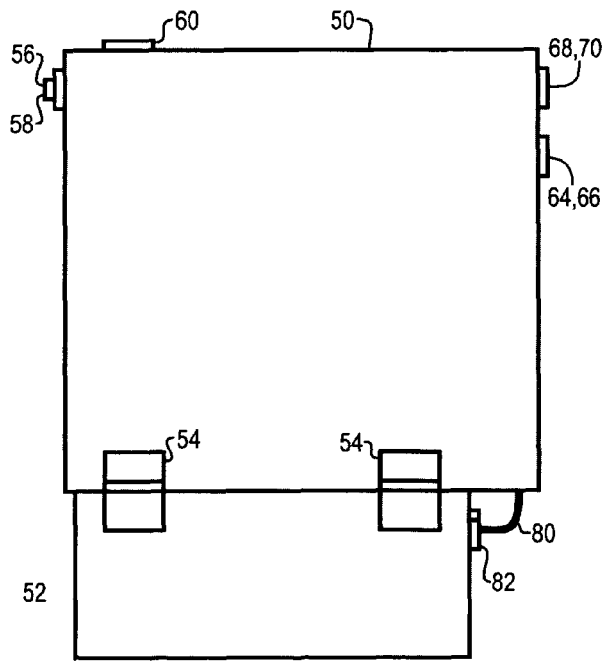
FIG. 7 is an end view drawing of a thermal therapeutic apparatus according to an illustrative embodiment of the present invention.
Figure 8:
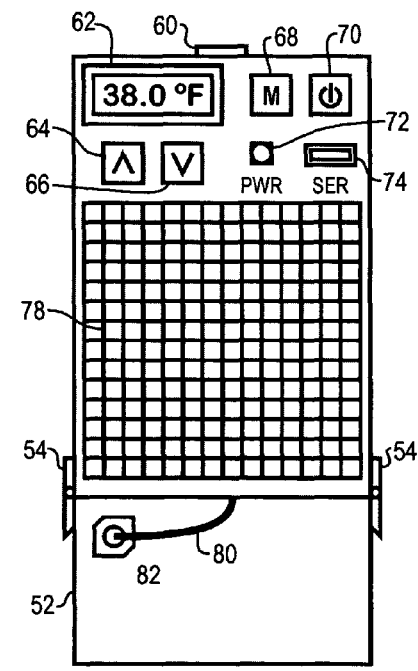
FIG. 8 is a side view drawing of a thermal therapeutic apparatus according to an illustrative embodiment of the present invention.

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope hereof and additional fields in which the present invention would be of significant utility.

The illustrative embodiments of the invention teach a portable body cooling and warming apparatus that enables users to access cold and heat therapy at fixed locations as well as when mobile, such as riding is a car, walking, and during other physical activities. A rechargeable battery power source and charger are provided in a body-worn thermoelectric cooling and heating apparatus so that users can draw power from conventional AC sources when available or the battery source while mobile. The apparatus can be belt-worn, worn using an over-the-shoulder strap, or worn using a backpack style carrier, or worn in a hip-supported configuration. Other portable carrying systems can be readily implemented as well. Flexible tubing couples the device to a thermal body wrap that is attached to the affected portion of the user's body.

Heat transfer is accomplished using a Peltier-effect thermoelectric heat pump. The thermoelectric ("TEM") heat pump is powered by direct current, which forces heat to flow from a cold side to a hot side of the TEM. In a cooling mode of operation, the cold side of the TEM is conductivity coupled to a fluid heat exchanger, which has a working fluid circulating therein. Heat is drawn from the working fluid as it circulates through the heat exchanger. A piezoelectric pump is used to force the working fluid to flow through the heat exchanger. Flexible tubing couples the working fluid from the pump and heat exchanger to a flexible body wrap. The body wrap includes fluid channels that direct the working fluid through a tortuous path, which is held in close proximity to an affected area of the user's body. Heat flows from the user's body to the working fluid by virtue of the body wrap's placement against the user's body. Thus, heat is removed from the user's body, flows away in the working fluid, and is removed by action of the TEM heat pump. In a heating mode of operation, the direct current flow to the TEM heat pump is reversed, which causes the flow of heat across the device to be reversed. In this mode of operation, heat is absorbed from the atmosphere by the heat sink, and is transferred to the user's body through the working fluid.

The body wrap can be any of a variety of types known to those skilled in the art. A pair of flexible conduits couple the body wrap to the apparatus of the present invention. The body wrap may be of the type employing a tortuous flow path or may be of the bladder type. Other types of body wraps known to those skilled in the art can be employed as well. The only requirement is that the body wrap accepts a flowing working fluid medium as the heat transfer mechanism. The flexible conduit may be conventional tubing, made from any suitable rubber or thermoplastic material.

Reference is directed to FIG. 1, which is a drawing of a shoulder-worn thermal therapeutic apparatus 4 according to an illustrative embodiment of the present invention. The illustration depicts a user 2 who is utilizing thermal therapy to the shoulder area using a body-worn shoulder pad 10. The pad 10 is coupled to the thermal therapeutic apparatus via two flexible hose type conduits 8. The apparatus 4 is slung from the opposite shoulder using a shoulder strap 6 support structure. A key to the successful utilization of the present invention is the compact size and light weight of the apparatus, as well as the portable power management, which enables the user to engage in an active life-style while still obtaining the needed thermal therapy.

Reference is directed to FIG. 2, which is a drawing of a belt-worn thermal therapeutic apparatus 14 according to an illustrative embodiment of the present invention. The user 12 is applying thermal therapy to an elbow joint using an elbow pad 20 thermal therapy pad. The pad 20 is coupled to the thermal therapy apparatus 14 using a pair of hoses 18. The thermal therapy apparatus 14 is supported by a belt type support structure 16. It should be noted that a given thermal therapy apparatus can be adapted to engage a variety of support structure types. This enables the user and caregiver to select a support system that is consistent with the needs and comfort of the user in any given application.

Reference is directed to FIG. 3, which is a drawing of a backpack-worn thermal therapeutic apparatus 24 according to an illustrative embodiment of the present invention. The user 22 is applying thermal therapy to a knee joint using a knee-type thermal therapy pad 32. A pair of flexible hose conduits 30 couple the knee pad 32 to the thermal therapy apparatus 24. A pair of should straps 26 and a waist belt 28 provide the necessary support structure to form the backpack style system. In many of the support structure embodiments, the apparatus and support structure elements are padded to provide comfort to the user. Canvas and synthetic materials are suitable for this purpose. The conduit hoses are insulated against the flow of heat so as to maintain the thermal efficiency of the system. The exterior of the body-worn pad is also insulated against the flow of heat.

Reference is directed to FIG. 4, which is a drawing of a computer programming station for a thermal therapeutic apparatus 34 according to an illustrative embodiment of the present invention. As noted hereinbefore, modern thermal therapy utilizes various temperatures and time internals for therapy. The present invention is adapted to deliver programmable set point temperatures for both heat therapy and cold therapy. In fact, a mixture of heat and cold therapy can be delivered in one therapeutic session. The present invention simplifies the programming operation, where various set-point temperatures and time intervals are entered into the apparatus 34, by providing a serial interface to a personal computing device. A serial cable 38 couples the apparatus 34 to a serial port on a personal computing device 36. Application software provided to the user with the apparatus 34 is loaded and executed on the computing device 36. A computer monitor 40 and a keyboard 42 facilitate the entry and display of specified temperature set points and time intervals.

Reference is directed to FIG. 5, FIG. 6, FIG. 7, and FIG. 8, which are a top view, coolant connector end view, side view, and user interface end view drawing of a thermal therapeutic apparatus according to an illustrative embodiment of the present invention. The apparatus is housed in a rigid housing 50 that is formed as a rectangular box-like structure. Other geometric configurations could be readily employed, and the corners and edges could be rounded to facilitate comfortable carrying by a user. A battery 52 is coupled to the bottom of the housing 50. Four latches 54 are employed to hold the battery in place. Any suitable connecting system could be used. In an alternative embodiment, the battery is inserted into the interior of the housing 50. The external battery is advantageous because it allows differing sizes of batteries to be used, depending on the amount of battery capacity needed for a particular application. Each battery 52 includes a DC power connector 82, which is coupled to a power supply (not shown) inside of the housing 50 by a power cable 80.

Since the apparatus transfers heat between the user and the atmosphere, there are relatively large vents with grills 76, 78 on the working fluid connector end and user interface end, respectively. The vents enable the free flow of atmospheric air through the apparatus. The coolant connector end of the housing 50 presents an inlet coolant connector 56 and an outlet coolant connector 58. In the illustrative embodiment, "o"-ring sealed quick connectors with automatic shut-off valve adapters are employed. This approach allows the user to easily connect the working fluid conduits that couple to the body-worn pad without leaking significant amounts of working fluid. In other embodiments, the working fluid conduits may be permanently attached, utilizing a closed system. In the illustrative embodiment, a coolant reservoir (not shown) is provided on the interior of the housing 50. The reservoir provides a reserve of working fluid and allows a small amount of air to accumulate in the fluid conduit system without adversely affecting system performance. A fill spout and cap 60 are present on the top of the housing 50. The fill cap 60 is removed to re-fill the coolant conduit system when needed.

The user interface of the apparatus is presented on the user interface end of the housing 50. In the illustrative embodiment, a digital display 62 is provided, which is used to display the present set-point temperature and elapsed time, as well as the programming set-point temperatures and time intervals during the programming of the apparatus. Touch key actuators 64, 66 are provided to increase and decrease the desired set-point temperature or the desired time interval during programming or during routine operation. A mode key actuator 68 is provided to select between different modes of operation, such as operation, programming, and diagnostic modes of operation. An on and off switch actuator 70 is provided for the customary purpose. A serial port 74 is provided for coupling to an external personal computing device to enable automated programming of the set point temperatures and time intervals, as well as other configuration parameters of the apparatus. In the illustrative embodiment, as USB serial port is contemplated, however any suitable computer interface known to those skilled in the art could be employed to achieve the needed interface to a computing device.

An external power connector 72 is provided for connection of an external power source. In the illustrative embodiment, an AC power transformer plugged into a wall outlet coupled to the utility power grid is one source of external power. Another source of external power is a coupling to the vehicular power adapter, or cigarette lighter socket on a motor vehicle. Those skilled in the art will appreciate that other power sources could be connected to the external power connector 72, provided that the correct voltage and current requirements for the system were met. In the illustrative embodiment, a nominal twelve-volt direct current source is used. However, the power supply (not shown) could be adapted to convert AC to DC power within the housing 50, so that AC external sources could then be coupled to the apparatus.

Figure 9:
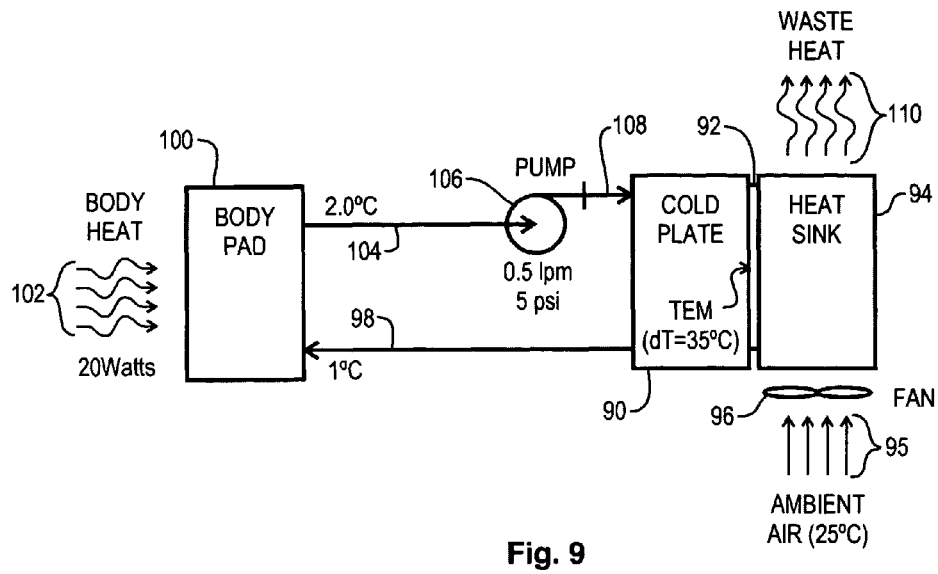
FIG. 9 is a heat flow diagram of a thermal therapeutic apparatus according to an illustrative embodiment of the present invention.

Reference is directed to FIG. 9, which is a heat flow diagram of a thermal therapeutic apparatus according to an illustrative embodiment of the present invention. As noted hereinbefore, an important advantage of the present invention is its ability to deliver a compact, powerful, man-portable device that provides sufficient run time to allow users to engage in reasonably active life styles while using the system. The illustrative embodiment provides at least twenty watts of cooling power for an estimated run time of three to four hours when the batteries are fully charged, at a differential temperature of thirty-five degrees Celsius. FIG. 9 graphically depicts this capacity in a heat flow diagram. The system includes the body pad 10, which is coupled by conduits 98 and 104 to the apparatus. The pump 106, cold plate manifold 90, TEM module 92, heat sink 94 and fan 96 are illustrated. In operation, working fluid is circulated within the conduits at a flow rate equal to or greater than one-half liters per minute through a pressure drop of five pounds per square inch. The fluid is cooled in the cold plate 90 and exits at a set-point temperature of one to two degrees Celsius, for example. The fluid is forced through the body pad 100, where heat is absorbed from the body at a rate of twenty watts, continuously. The fluid experiences a temperature gain of approximately one degree Celsius as it passes through the body pad 100. Thus, the fluid is returned to the cold plate 90 at that temperature.

The cold plate 92 removes heat from the fluid at a rate slightly greater than twenty watts, so the fluid is reduced back to two degrees Celsius to for further circulation. The heat is removed from the cold plate 92 by the Peltier effect of the TEM module 92. Since the ambient temperature is a nominal twenty-five degrees Celsius, and since the heat sink differential with respect to ambient is about ten degrees Celsius, by virtue of the forced convection induced by the fan, the differential temperature of the TEM module is about thirty-five degrees Celsius. In the illustrative embodiment, four twenty-nine watt (maximum cooling capacity) TEM modules are employed that have maximum current and voltage parameters of three amps and seventeen volts, respectively. The power source is a nominal twelve volt system, with a power supply adjusting current flow to meet the predetermined set-point temperature requirement. When working across a differential temperature of thirty-five degrees Celsius, these modules' combine heat transfer capacity is twenty-eight watts. Thus, a performance margin is realized for the twenty-watt design goal. In one embodiment, Advanced Thermoelectric (Nashua, N.H.) model No. ST-127-1.0-3.0 TEM modules are contemplated. Other manufacturers provide similar modules, which may be considered by those skilled in the art. In FIG. 9, the ambient air 95 is heated as it passes through the heat sink 94, and is exhausted together with the waste heat 110.

Figure 10:
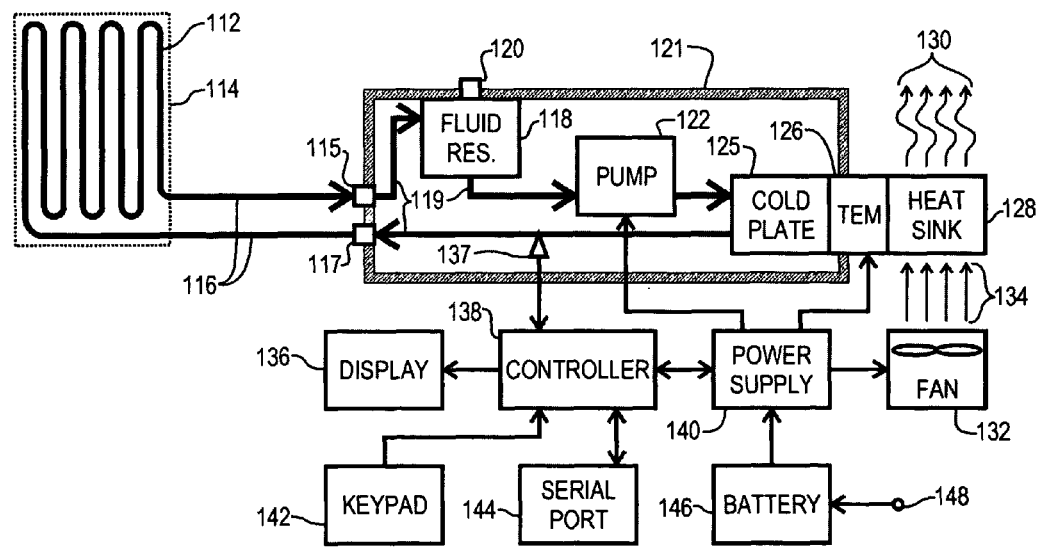
FIG. 10 is a functional block diagram of a thermal therapeutic apparatus according to an illustrative embodiment of the present invention.
Figure 11:
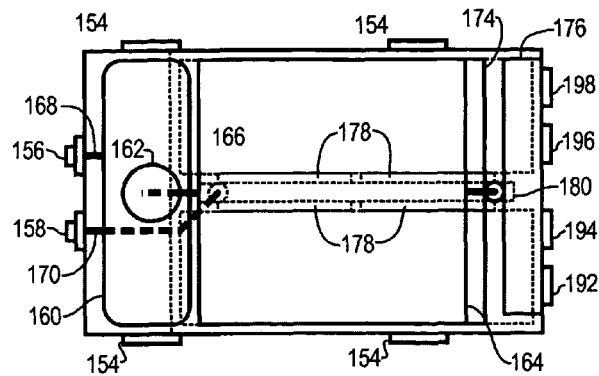
FIG. 11 is a top view of the internal components in a thermal therapeutic apparatus according to an illustrative embodiment of the present invention.
Figure 12:
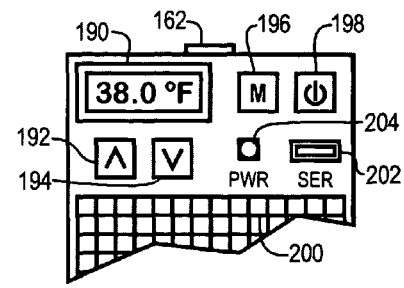
FIG. 12 is a partial end view illustrating the user interface of a thermal therapeutic apparatus according to an illustrative embodiment of the present invention.
Figure 13:
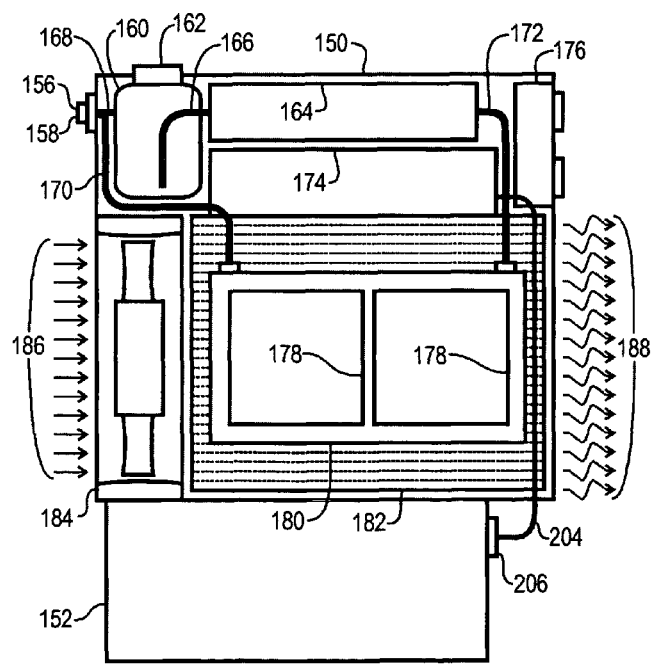
FIG. 13 is a side section view of the internal components in a thermal therapeutic apparatus according to an illustrative embodiment of the present invention.
Figure 14:
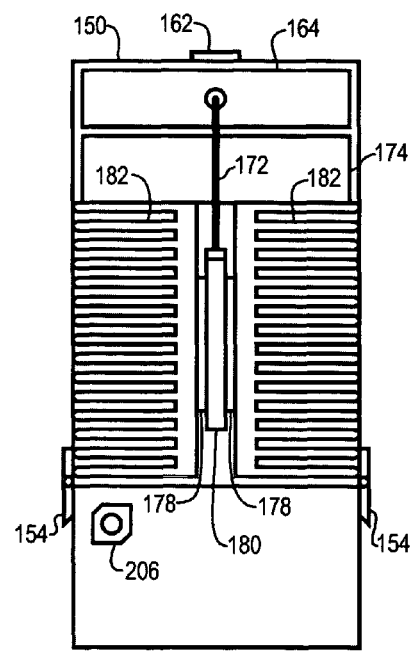
FIG. 14 is an end view of the internal components in a thermal therapeutic apparatus according to an illustrative embodiment of the present invention.

Reference is directed to FIG. 10, which is a functional block diagram of a thermal therapeutic apparatus according to an illustrative embodiment of the present invention. This diagram illustrates the various functional component used in the illustrative embodiment. The body-worn pad 114 has the conduit 112 arranged in a tortuous path inside. Coupling conduits 116 connect to fluid connectors 115, 117. In the illustrative embodiment, a blend of water and ethylene glycol are used as the working fluid. Other fluids, including pure water may be use. Those skilled in the art are familiar with suitable heat transfer working fluids and their properties. The remaining components comprise the apparatus, most of which are enclosed in a single housing (not shown), that may be fabricated from plastic, aluminum, or other suitable lightweight materials, as are known to those skilled in the art. The fluid circuit of the apparatus includes several pieces of connecting conduit 119 that couple together the fluid reservoir 118, the pump, and the cold plate manifold 125, which is thermally coupled to the TEM module 126. The fluid circuit is insulated against the flow of heat by insulation 121. A plastic cellular-type insulation 121 is employed in the illustrative embodiment, although any suitable insulation know to those skilled in the art may be employed. The insulation may also form the padded enclosure in one embodiment. The fill cap 120 of the fluid reservoir 118 extends through the insulation 121 so that the user can replenish the fluid when needed.

The pump 122 in the illustrative embodiment is a piezo-electric pump, which is selected for its compact size, lightweight, and power efficiency. The pump was developed by Deak Technologies (Hudson, Mass.), and is identified as a DTI-500 series pump. The power supply driving the pump is a twelve-volt nominal oscillating wave, which drives the piezoelectric crystal to in duce movement the fluid. The flow rate of the pump is controlled by the frequency and amplitude of the oscillating wave. The power supply 140 is adapted to provide the requisite oscillating wave under control of controller 138. The cold plate manifold 125 is fabricated from aluminum with channels formed therein to form the manifold cavities. The cold plate manifold 125 is thermally bonded to the TEM modules 126 using thermal greases, as are known to those skilled in the art. The opposite side of the TEM module 126 is thermally bonded to a pair of finned heat sinks 128. The heat sinks 128 are thermally coupled to the ambient atmosphere by forced convection induced by boxer fan 132. Those skilled in the art are familiar with heat sink design and heat transfer concepts. Ambient air 134 is forced by fan 132 through the heat sink fins 128, and is exhausted together with the waste heat 130.

The electrical components of the apparatus may be located outside of the insulation 121, but still within the apparatus housing. This arrangement is advantageous since some heat is produced by the electronic components. The power supply 140 is a solid-state type, which provides direct current to the TEM modules 126. The current flow to the TEM modules is adjusted by the controller 138, so that the output temperatures of the cold plate 125 can be driven to the predetermined set point temperatures. The temperature of the working fluid is sensed by temperature sensor 137. The temperature sensor may be a thermal junction type, a thermistor, or other type of sensor device, as are known to those skilled in the art. The controller 138 controls the power supply to drive the fan 132 and the pump 122 during operation of the apparatus. A liquid crystal display 136 and key-matrix keypad of actuators are also coupled to the controller, and are used in the aforementioned user interface functions. A USB compliant serial port 144 is coupled to the controller, and is used to communicate with an external personal computing device for programming and control applications.

The battery 146 in the illustrative embodiment is a twelve-volt nominal lithium-ion rechargeable battery. The capacity is approximately one hundred eighty watt-hours, which yields a typical run time of three hours in cooling mode, longer in heating mode. In the illustrative embodiment, an Ultralife Batteries, Inc. (Newark, N.Y.) model UBI-2590 battery is used. The battery is latched to the exterior surface of the housing. An external charging contact 148 is provided for coupling utility grid power or DC power form a vehicular connector.

Reference is directed to FIG. 11, FIG. 12, FIG. 13, and FIG. 14, which are a top section view, a user interface detail, am side sectional view and an end sectional view of the internal components in a thermal therapeutic apparatus according to an illustrative embodiment of the present invention. The four TEM modules 178 are located near the center of the housing 150, and are thermally bonded to the cold plate manifold 180 and the twin finned heat sinks 182. A boxer fan 184 is positioned at one end of the heat sinks 182, and forces atmospheric air 186 through the fins of the heat sinks 182. Heat is transferred to or from the air, which exits 188 the opposite end of the housing 150. Vents are formed into both ends of the housing 152, and are protected by grills 200. The cold plate manifold 180 is couple to the working fluid conduits. The pump 164 draws fluid from the fluid reservoir 160 through conduit 166. The pump discharges the fluid into conduit 172, which feeds the inlet end of the cold plate 180. The fluid circulates within the cold plate manifold 180, and exits through conduit 170. Conduit 170 is coupled to fluid outlet connector 158. Fluid inlet connector 156 couples the fluid to the fluid reservoir 160. Connecting the body worn pad (not shown) to the fluid connectors 156, 158 completes the fluid conduit circuit. A fill cap 162 of the fluid reservoir is presented on the top surface of the housing 150, for filling the fluid conduit circuit.

The controller, power supply, and other electrical circuitry are located in area 174. The user interface circuitry is located in area 176. A battery cable 204 couples the electrical circuitry 174 with the battery 152 through battery connector 206. The user interface consists of the display 190, the up and down selector actuators 192, 194, the mode switch actuator 196, the power switch 198, and external power connector 204, and the serial port interface connector 202. The functions of these components were described hereinbefore. Note that the packaging of the apparatus is tight and efficient, enabling a system that is compact and portable, as well as light weigh for convenient user portability.

Figure 15:
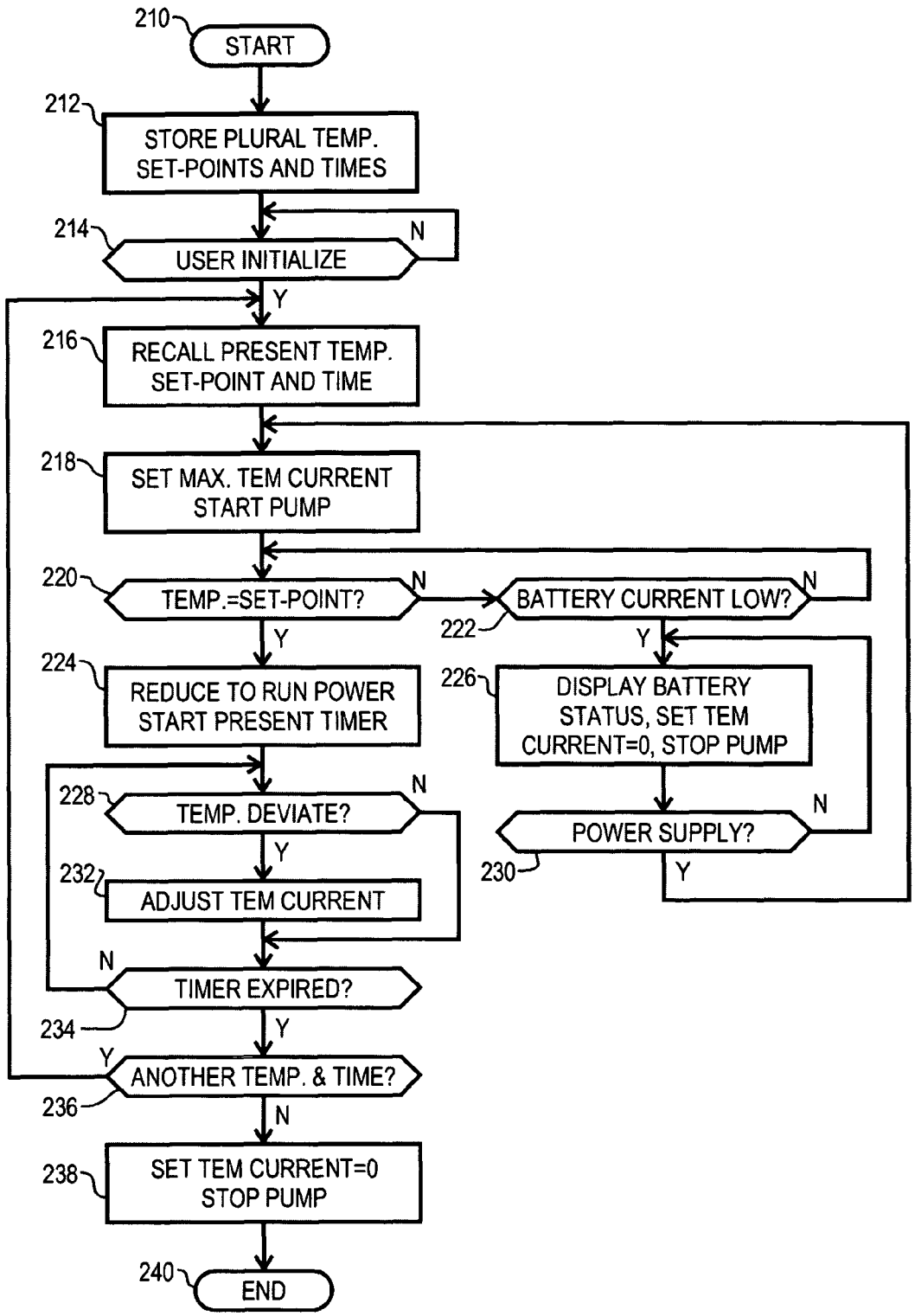
FIG. 15 is an operational flow diagram of a method of operating a thermal therapeutic apparatus according to an illustrative embodiment of the present invention.

Reference is directed to FIG. 15, which is an operational flow diagram of a method of operating a thermal therapeutic apparatus according to an illustrative embodiment of the present invention. The method depicted in FIG. 15 is that of a multiple temperature set point and time interval therapeutic session. The process begins at step 210 and proceeds to step 212. At step 212, the plural temperature set points and time intervals are stored into a memory of the controller. This data can be input through the user interface with key actuations, or it can be transferred through the serial port interface from a personal computing device. At step 214, the process checks for user initialization of a therapeutic session. This is accomplished using the mode key actuator in the illustrative embodiment. If the user has initialized a session flow proceeds to step 216.

At step 216, the controller recalls a present temperature set point and time interval. The times and temperatures are stored in a memory queue, and are recalled in sequence, with the top data set referred to as the "present" temperature and time. At step 218, the controller sets the TEM current and polarity, using the highest current setting so that the target set-point temperature can be reached as quickly as possible. At step 220, the controller reads the temperature sensors, which indicates the actual fluid temperature. If the set-point temperature has not yet been met, flow proceeds to step 222. At step 222, the controller checks that battery condition. If the battery condition is not low, flow returns to step 220, where the temperature check is repeated. If the battery condition is low at step 222, then flow proceeds to step 226. At step 226, the controller displays the low battery condition to the user and reduces the TEM current to zero, stopping both the pump and the fan as well. At step 230, at test is made to see if the user has attached an external power supply in response to the alert indication. If the user has not yet attached external power, flow returns to step 226 to renew the alert. If the user has attached power, then flow returns to step 220, to again determine in the target set point temperature has been reached.

Again considering step 220, if the controller determines that the present set-point temperature has been reached, then flow continues to step 224. At step 224, the controller reduces the run current from maximum current, since the target temperature has new been reached, and starts the present interval timer. Note that the timer is not started until the target set-point temperature is reached. This insures that the patient receives a full measure of treatment. At step 228, the controller rechecks the measured temperature. If the temperature has drifted from the set point, then the current is adjusted correspondingly at step 232. On the other hand, at step 228, if the temperature has not drifted, then flow proceeds to step 234. At step 234, the process checks to see if the present timer has expired. If not, then flow returns to step 228 to recheck the temperature. If the timer has expired at step 234, then the process checks to see if there is another temperature and time data pair in the memory queue at step 236. If there is, that data is recalled at step 216, where the new temperature and time are acted upon as just described. On the other hand, at step 236, if the there are no more temperature and time data remaining, then the process shuts of the apparatus at step 238 and exits the process at step 240.

Figure 16:
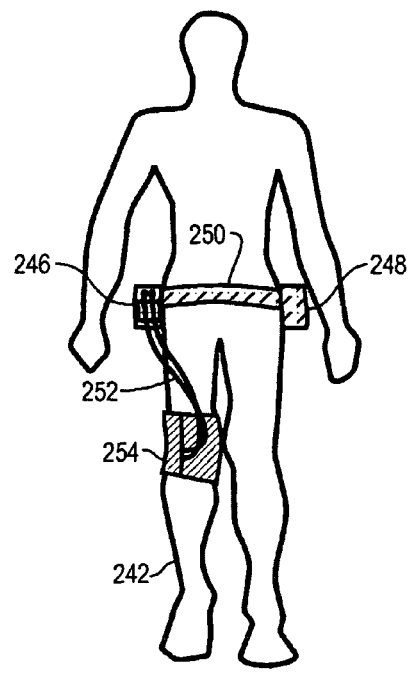
FIG. 16 is a drawing of a belt-worn thermal therapeutic apparatus according to an illustrative embodiment of the present invention.

Reference is directed to FIG. 16, which is a drawing of a belt-worn thermal therapeutic apparatus according to an illustrative embodiment of the present invention. The apparatus in FIG. 16 separates the functional components of the apparatus into two groups so that they can be positioned along difference portions of the support structure. This approach advantageously distributes both the bulk and weight of the apparatus for more comfortable wear and use. In particular, the user 242 wears a belt 250, which has a first portion 246 and a second portion 248 of the apparatus distributed there about. The fluid components are located in the first portion 246. A pair of flexible hose conduits 252 coupled the working fluid between the first portion 246 and the body-worn pad 254, which is a knee pad in the illustrative embodiment.

Figure 17:
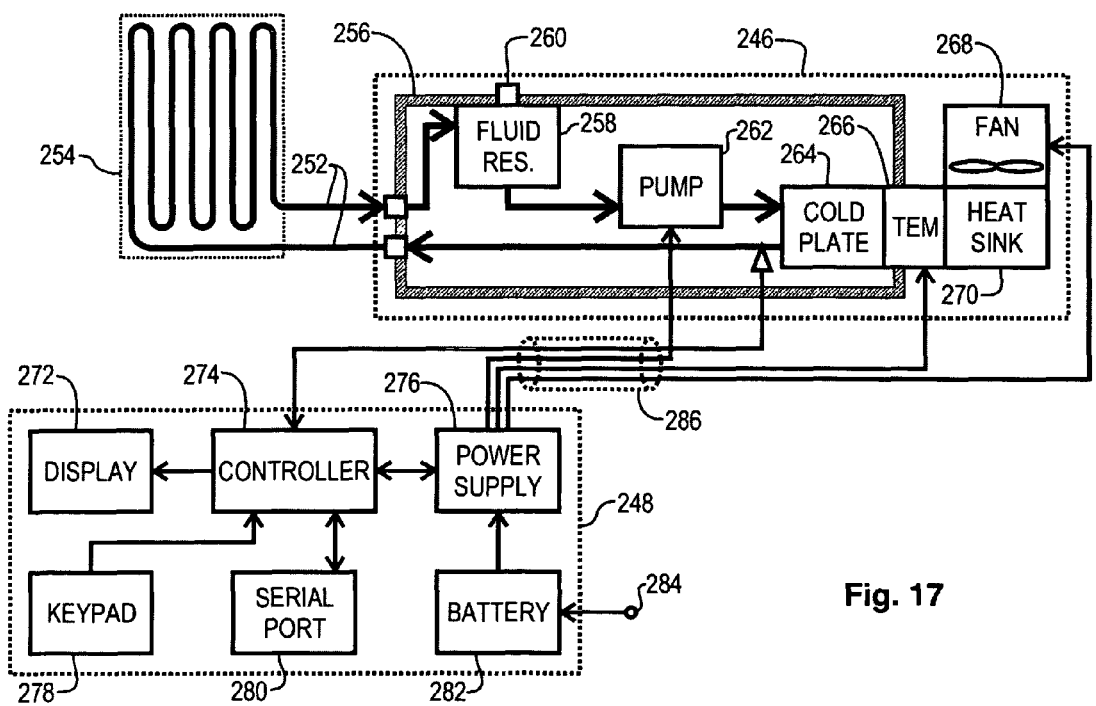
FIG. 17 is a functional block diagram of a two enclosure thermal therapeutic apparatus according to an illustrative embodiment of the present invention.

FIG. 17 is a functional block diagram of a two enclosure thermal therapeutic apparatus according to the illustrative embodiment of the present invention illustrated in FIG. 41. In FIG. 42, the first portion, or enclosure, 246 houses the fluid reservoir 258, the pump 262, the TEM 266, with cold plate manifold 264 and heat sink 270, and the fan 268. The fluid conduit circuit is insulated 256 against the flow of heat. The body worn pad 254 is coupled to the second portion 246 with a pair of conduit hoses 252. The second portion enclosure 248 is coupled to the first portion enclosure 248 by a bundled 286 of electrical conductors that couples power and control circuits between the two portions. The second portion 248 houses the controller 274, the power supply 276, the battery 282, the display 272, the keypad 278, the serial port 280, and the external power connector 284. The functions of the various components is essentially the same as described regarding the corresponding components in FIG. 10, and will not be repeated here.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A portable thermal therapeutic apparatus, for transferring heat with a creature using a heat transfer fluid circulating within a conduit held in contact with the creature, and adapted to receive power from a battery; file apparatus comprising: a housing adapted to engage a support structure worn by the creature during portable use of the apparatus; a thermoelectric heat pump, disposed within: said housing, operable to transfer heat at a rate proportional to the amount of electric current driving said thermoelectric heat pump, between an atmospheric heat sink and a manifold having fluid channels formed therein; a piezoelectric pump coupled to circulate the heat transfer fluid through said manifold and the conduit; a power supply having a battery connector for receiving electric current from the battery; and a control circuit coupled to said power supply and coupled to provide electric current to drive said thermoelectric heat pump, and having a temperature sensor positioned near a fluid channel of said manifold, said control circuit operable to adjustably control the rate at which electric current drives said thermoelectric heat pump in response to said temperature sensor, thereby enabling the apparatus to achieve a predetermined set-point temperature of the heat transfer fluid, and further enabling the apparatus to maintain said predetermined set-point temperature over time.

2. The apparatus of claim 1 wherein said housing comprises an insulated portion.

3. The apparatus of claim 2, wherein a portion of said power supply and said control circuits are located outside of said insulated portion of said housing.

4. The apparatus of claim 1 wherein said support structure comprises at least one of a shoulder strap worn to engage a shoulder of the creature and a belt worn to engage a waist of the creature.

5. The apparatus of claim 1 wherein said control circuit is operable to reverse the polarity of said power supply, thereby reversing the heat flow through said heat pump.

6. The apparatus of claim 1 wherein said housing is divided into a first housing portion attached to a first location along said support structure and a second housing portion attached to a second location along said support structure, and wherein said piezoelectric pump and said thermoelectric heat pump are located within said first housing portion, and said power supply is located in said second housing portion.

7. The apparatus of claim 1, wherein said thermoelectric heat pump comprises plural thermoelectric heat pumps.

8. The apparatus of claim 1, further comprising a fluid reservoir disposed within said housing, and coupled between said manifold and said piezoelectric pump.

* * * * *